United States Patent [19]

Reichle

[11] 4,238,627
[45] Dec. 9, 1980

[54] OXIDATIVE PROCESS FOR PREPARING SUBSTITUTED BIPHENOLS

[75] Inventor: Walter T. Reichle, Warren, N.J.

[73] Assignee: Union Carbide Corporation, New York, N.Y.

[21] Appl. No.: 961,472

[22] Filed: Nov. 16, 1978

[51] Int. Cl.³ .................... C07C 37/00; C07C 37/11
[52] U.S. Cl. .................... 568/730; 568/718; 568/721
[58] Field of Search .................... 568/730, 718, 721

[56] References Cited

U.S. PATENT DOCUMENTS

| | | | |
|---|---|---|---|
| 2,885,444 | 5/1959 | Fookes et al. | 568/730 |
| 3,153,098 | 10/1964 | Boag | 260/620 |
| 3,562,338 | 2/1971 | Zaweski | 260/620 |
| 3,631,208 | 12/1971 | Hay | 260/619 R |
| 3,873,627 | 3/1975 | Lee et al. | 568/730 |
| 4,070,383 | 1/1978 | Rutledge | 568/730 |
| 4,085,124 | 4/1978 | Rutledge | 260/620 |
| 4,086,253 | 4/1978 | Hopper et al. | 260/396 N |
| 4,093,598 | 6/1978 | Banucci et al. | 260/47 ET |
| 4,096,190 | 6/1978 | Rutledge | 568/730 |
| 4,098,766 | 7/1978 | Rutledge | 528/317 |
| 4,098,830 | 7/1978 | Rutledge | 568/730 |
| 4,100,202 | 7/1978 | Rutledge | 568/730 |
| 4,100,203 | 7/1978 | Rutledge | 568/730 |
| 4,100,204 | 7/1978 | Rutledge | 568/730 |
| 4,100,205 | 7/1978 | Rutledge | 568/730 |
| 4,100,206 | 7/1978 | Rutledge | 568/730 |
| 4,101,561 | 7/1978 | Rutledge | 568/730 |
| 4,108,908 | 8/1978 | Rutledge | 568/730 |
| 4,132,722 | 1/1979 | Rutledge | 568/730 |
| 4,139,544 | 2/1979 | Rutledge | 568/730 |

FOREIGN PATENT DOCUMENTS 566274  5/1974  Switzerland .................... 568/730

*Primary Examiner*—Norman Morgenstern
*Attorney, Agent, or Firm*—Donald M. Papuga

[57] ABSTRACT

An oxidative process for preparing 4,4'-bis(2,6-dihydrocarbylphenols) is provided which comprises contacting with good agitation a disubstituted phenol such as 2,6-di-tertiarybutyl phenol with up to stoichiometric amounts of oxygen in the presence of a small catalytic quantity of a catalyst selected from the group consisting of alkali metal and alkaline earth metal hydroxides, alkali metal and alkaline earth metal salts of a weak acid, amine bases, and mixtures of the same at a temperature from about 50° to 240° C. until a reaction product containing a substantial amount of the corresponding biphenol is formed, said reaction product being substantially free of quinones.

16 Claims, No Drawings

OXIDATIVE PROCESS FOR PREPARING SUBSTITUTED BIPHENOLS

The present invention relates to a process for making biphenols and, more particularly, to a process whereby a substituted phenol is directly oxidized to the corresponding substituted biphenol.

Biphenols, and particularly substituted biphenols, have found wide utility as bactericides, chemical intermediates, copolymers, and antitoxidants. For example, biphenols, especially those from 2,6-disubstituted phenols, are used to stabilize such materials as animal and vegetable fats or oils, gasoline, lubricants, rubber compositions and the like. Moreover, 4,4'-biphenol, which can be prepared by dealkylation of substituted biphenols, has been found to be of interest as a comonomer in the preparation of various condensation polymers and copolymers.

Heretofore, the manufacture of biphenols has generally first involved the oxidation of various substituted phenol reactants in the presence of metallic or high concentrations of strongly alkaline catalysts forming the corresponding diphenoquinones. This diphenoquinone is recovered and may then be reduced with a reducing agent, such as hydrogen or the excess of a phenol, to the desired biphenol.

A more recent process disclosed in U.S. Pat. No. 3,562,338 to Zaweski, eliminates the need to separate intermediate reaction products formed by oxidation of a substituted phenol prior to the final reaction step wherein the substituted biphenol is prepared. In this process, a substituted phenol is reacted with an oxygen containing gas in the presence of an alkali metal hydroxide until substantially all the phenol has been oxidized to the diphenoquinone. A second portion of substituted phenol is then added to the reaction mixture produced during the oxidation reaction, and the mixture is heated to a temperature of from about 100° C. to 350° C. in the substantial absence of oxygen and maintained at this temperature until a reaction product containing a substantial amount of substituted biphenol is formed. This process, however, must be carried out in two stages and would not generally be suitable for the continuous production of biphenols.

Also recently disclosed, for example, in U.S. Pat. Nos. 4,085,124 and 4,096,190 to Rutledge, are processes for oxidative coupling of alkylphenols and the like to directly prepare dimers thereof, wherein the coupling reaction is carried out in an aqueous medium in the presence of an alkaline material and various amine complex catalysts. While the process is disclosed as directly preparing the phenol dimer without the need to further react intermediate reaction products, the products formed thereby contain a mixture of dimers from which the desired biphenol must then be separated.

A process that could be used to directly produce only the biphenols in a one step process, or would provide a more economical means for preparing the biphenol, would be highly desirable. Especially advantageous would be a process that could be used for the continuous preparation of biphenols.

In accordance with the present invention there is provided a one step process for making 4,-4'-bis(2,6-disubstitutedphenols), and which process may in a preferred embodiment thereof be employed for the continuous preparation of such biphenols. The process of the invention comprises contacting a phenol having the formula:

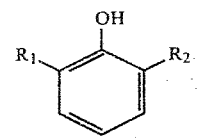

wherein $R_1$ and $R_2$ is a member selected from the group consisting of alkyl radicals containing from 1 to 20 carbon atoms, aryl radicals containing from 6 to 14 carbon atoms, aralkyl radicals containing from 7 to 9 carbon atoms, and cyclic alkyl group, wherein $R_1$ and $R_2$ may be the same or different, with oxygen or an oxygen containing gas in the presence of a small catalytic quantity of a catalyst selected from the group consisting of alkali metal hydroxides, alkali metal salts of a weak acid, alkaline earth metal hydroxides, alkaline earth metal salts of a weak acid, amine bases, and mixtures of the same at an elevated temperature, for example, from about 50° C. to about 240° C., and preferably from the melting point of the reaction mixture to about 220° C., until up to, and preferably less than a stoichiometric amount of oxygen reacts with said phenol and a reaction product is formed that contains a substantial amount of 4,4'-bis-(2,6-di-hydrocarbylphenols). The oxidation reaction readily proceeds to prepare the desired biphenols while the reaction product of said oxidation reaction is surprisingly and unexpectedly substantially free of quinones.

In a preferred embodiment of the invention, it has been found that if at least a small amount, and preferably at least about 0.01 weight percent of water or of a lower hydroxyl containing alkyl compound, based on the weight of reactants, is present in the initial reaction mixture, the oxidation reaction will be initiated without any delay or inhibition period, a feature which is especially advantageous in a continuous process for preparing the biphenol reaction product.

The process is readily conducted by placing the phenol and other reaction mixture components in a reaction vessel having agitation means, or can be advantageously carried out to continuously produce biphenols by, for example, passing phenol through appropriate reaction tubes and simply contacting the same with oxygen or an oxygen containing gas and catalyst in a manner to be more fully described hereinafter. The oxidation reaction should be carried out with agitation, and preferably with vigorous agitation, or by using other means that affords intimate contact between the oxygen containing gas and the reaction mixture.

The phenols which may be employed as starting materials in the process of the invention are phenols having the general formula

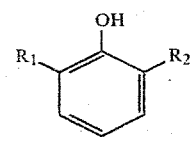

wherein $R_1$ and $R_2$ may be the same or different radicals selected from the group consisting of alkyl radicals containing from 1 to 20 carbon atoms, aryl radicals containing from 6 to 14 carbon atoms, aralkyl radicals containing from 7 to 9 carbon atoms, and cyclic alkyl cyclic group. Typical phenols that may be employed are:

6-tert-butyl-o-cresol
2,6-di-sec-butyl phenol
6-sec-eicosyl-o-cresol
2-butyl-6-cyclohexylphenol
6-cyclohexyl-o-cresol
6-(2-methylbenzyl)-o-cresol
2,6-di(α-methylbenzyl)phenol
2-sec-butyl-6-(α-methylbenzyl)phenol
6-phenyl-o-cresol
2,6-diisoproplphenol
6-isopropyl-o-cresol
and preferably
2,6-di-tert-butyl phenol.

An essential component of the reaction mixture is a catalytic amount of a catalyst, the suitable catalysts being selected from the group consisting of alkali metal hydroxides, alkali metal salts of a weak acid, alkaline earth metal hydroxides, alkaline earth metal salts of a weak acid, amine bases, and mixtures of the same. Illustrative of suitable catalysts are sodium hydroxide, potassium hydroxide, barium hydroxide, rubidium hydroxide, cesium hydroxide, potassium carbonate, sodium carbonate, cesium carbonate, rubidium carbonate, potassium sulfite, sodium borate, potassium acetate, diazabicyclononane, pyridine, tetramethylguanidine, and 1,4-diazabicyclo-(2,2,2)-octane (DABCO). Most suitable and preferred are potassium carbonate or diazabicyclooctane (DABCO).

The amount of catalyst used is not narrowly critical, but only a small amount is sufficient to promote dimerization of the phenols. In general, the amount used is as little as about 0.1 weight percent, through amounts up to about 1 weight percent are useful, and even greater amounts of catalyst may be used if desired.

In a preferred embodiment of the process of the invention, at least a small amount of water or of a hydroxy containing lower alkyl compound such as ethyl or methyl alcohol is added to the reaction mixture. It has been found that the process of even small amounts of said additive may be sufficient to eliminate the delay or induction period of the oxidative dimerization reaction but the amount that may be used is not narrowly critical. As a rule, the amount used is at least about 0.01 weight percent of the reaction mixture but greater amounts may be used if desired. The material may be added to the reaction mixture as a separate component or may be advantageously used to prepare a solution of the herein described catalyst prior to adding to the reaction mixture.

In the practice of the invention the amount of oxygen employed relative to the phenol is quite critical. In general, only an amount of oxygen up to that stoichiometrically required for the direct oxidative dimerization of a disubstituted phenol to the corresponding biphenol according to the following general reaction should be used, but it is preferred to use less than that stoichiometrically required:

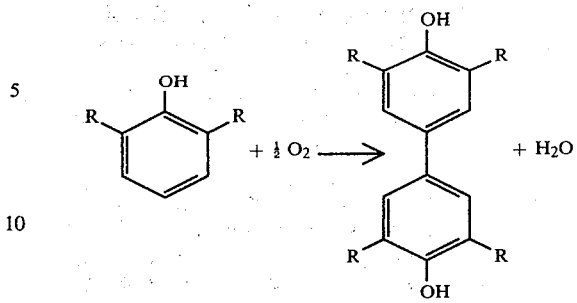

The reaction is conducted, for example, by passing oxygen, and preferably an oxygen containing gas such as air, through the reaction mixture in a reaction vessel with agitation to obtain intimate contact of the reactants. The reaction can be conducted at atmospheric pressure or at higher pressures, with moderate pressures up to about 300 psig being preferred. A most useful pressure range is from about 50 psig to about 200 psig. To insure that the amount of oxygen reacting with phenol does not exceed that stoichiometrically required, as hereinabove shown, the amount of oxygen in contact with the phenol can be, in general, controlled by limiting the flow of gas through or into the reaction vessel. Alternatively, it is sometimes advantageous to introduce amounts of oxygen or oxygen containing gas greater than that stoichiometrically required for the amount of phenol present, and to limit the amount of oxygen which actually reacts with the phenol by control of contact time between the reactants and/or choice of type and concentration of catalyst and reaction temperature.

The reaction can be conducted at a temperature from about 50° C. to about 240° C., and preferably at a temperature that ranges from the melting temperature of the reaction mixture (generally about 175° C. to 180° C.) to about 200° C. The use of a solvent for the reaction mixture is not generally required or preferred, though, if desired, a solvent may be added with the phenol to the reaction vessel. Useful solvents comprise hydrocarbons having high boiling points of from about 80° C. to 200° C., such as the aromatic hydrocarbons benzene, toluene, xylene, mesitylene, or saturated hydrocarbons (paraffins) and the like.

The process should be carried out for the time sufficient to convert substantially all of the phenol reactant to the corresponding biphenol. The length of time for optimum yield will depend upon the reaction temperature, type and amount of catalyst and induction period for the reaction. In general excellent yields of biphenol are obtained in from about 30 minutes to about one hour.

Conversion of phenol to the corresponding biphenol in accordance to the practice of the invention will result in substantially no by-product formation, including the formation of substantially no quinones. The biphenol product can be readily recovered from the reaction mixture with generally only the separation of unreacted phenol and some water from the biphenol being necessary.

If desired, the process may alternatively be conducted to continuously produce biphenols in high yield. A suitable continuous reactor generally consists of a length of vertically mounted reactor tubing having heating or cooling means surrounding it. A suitable packing medium, such as metal packing or metal or glass beads, is used inside the vertical tube and separate reactor streams are controlably fed into the reactor tube, preferably to the top thereof to produce a co-current down-flow reaction mode therein. Conversion rates/pass from about 20 to about 60%, based on the phenol, have been obtained at a reaction temperature of about 200° C., with catalysts such as potassium carbonate or DABCO and water being added to the reactant stream.

Recycling of the reactant stream may be done, if desired, since the reaction mixture is substantially free of any by-products including quinones, or the biphenol may be readily recovered from the reactant stream before reusing the unreacted phenol.

The invention will become more clear when considered together with the following examples which are set forth as being merely illustrative of the invention and which are not intended, in any manner, to be limitative thereof. Unless otherwise indicated, all parts and percentages are by weight.

EXAMPLE 1

A mixture of 200 grams (0.968 moles) of 2,6-di-tert.butyl phenol and 2 grams of a 50 percent aqueous potassium hydroxide solution was prepared in an autoclave reactor vessel having magnetically driven agitation means and temperature controlling means. The vessel was closed and brought to a temperature of about 180° C. Pure oxygen was admitted to a 100 psig internal pressure while agitation (about 460 rpm) was imparted to the reaction mixture. Initially, a mild exotherm took place (temperature increased to about 200° C.) along with a rapid oxygen pressure drop (to 75 psig). The pressure was brought back to 100 psig by adding oxygen several times within a 35 minute reaction time.

After the 35 minute reaction time, the reactor was vented and, upon cooling, the contents were discharged. 197 grams of a brown crystalline reaction product was recovered which analysis thereof showed that 75 percent of the substituted phenol had been converted to the corresponding 4,4'-biphenol dimer.

EXAMPLE 2

A 1000 cc reactor which was capable of accommodating 2000 psi pressure with high speed (1050 rpm) stirring means equipped with an external electrical heating mantle, thermocouple well and gas inlets was used in this example. 500 grams (1.94 moles) of 2,6-di-tert.butyl phenol and 6 grams of a 50 percent aqueous potassium hydroxide solution were charged into the reactor vessel and the reactor was then closed and brought to a temperature of about 185° to 190° C. Oxygen was then admitted to a pressure of 100 psig while the reactor contents were vigorously agitated. The reaction commenced at once as evidenced by a rapid temperature rise to about 210° to 215° C. and a sharp drop in pressure to about 75 psig. As the reaction proceeded, the oxygen pressure was brought back to the initial 100 psig pressure several times during the reaction and the temperature slowly dropped as the reaction rate decreased. After 30 minutes, the reactor was quickly vented and the reactor contents were cooled and discharged. An analysis of the crude reaction product showed a conversion of substituted pehnol to corresponding dimer of 55.7 percent. Substantially no impurities (<1%) were found, the biphenol dimer being the only product.

Using the procedure hereinabove described, a reaction was carried out with a charge of 500 grams of 2,6-di-tert.butyl phenol and 3.6 grams of an aqueous 50 percent solution of sodium hydroxide and oxygen for 30 minutes. An analysis of the reaction product showed a conversion of phenol to biphenol of about 54 percent with substantially no impurities being found.

Using the procedure hereinabove described a reaction employing a solution of 1.3 grams lithium hydroxide in 12 grams of water as catalyst and 500 grams of 2,6-di-tert.butyl phenol resulted in a conversion of phenol to dimer of 11 percent after 30 minutes.

EXAMPLE 3

By a procedure analogous to that described in Example 2, a series of reactions were carried out with 2,6-di-tert.butyl phenol, potassium carbonate and oxygen. The composition and proportions of reactants, pressure and temperature ranges, reaction time and biphenol yield were as follows:

| Run | Phenol (grams) | K$_2$CO$_3$ (grams) | Water (grams) | Temp. Range (°C.) | Pressure Range (psig) | Biphenol Yield (%) | Time (min) |
|---|---|---|---|---|---|---|---|
| 1 | 500 | 0 | 0 | 188–191 | 90 | 14.8 | 38 |
| 2 | 500 | 0 | 10 | 182–192 | 75–100 | 9.5 | 29 |
| 3 | 500 | 5.0 | 0 | 191–212 | 110–175 | 68.8 | 23 |
| 4 | 500 | 5.0 | 5.0 | 194–216 | 175–190 | 61.6 | 22 |
| 5 | 500 | 1.0 | 1.0 | 188–94 | 200–250 | 78.1 | 41 |
| 6 | 500 | 1.0 | 1.0 | 188–202 | 250–300 | 77.5 | 35 |
| 7 | 500 | 1.0 | 1.0 | 183–98 | 150–200 | 64.1 | 54 |
| 8 | 500 | 1.0 | 1.0 | 224–247 | 200–250 | 50.0 | 17 |

The water and potassium carbonate were added to the reactor as a solution. The crude reaction product obtained from each of Runs 3 to 7 were light yellow in color as contrasted to the highly colored, dark brown product obtained when a caustic catalyst is employed.

In carrying out Run No. 3, it was observed that the reaction did not start up immediately, and only after about 2 minutes had passed did signs of the reaction start up occur.

In Run No. 1 neither catalyst nor water was added. The reaction rate was very slow and an inhibition period of about 2 minutes was observed. The crude reaction product, which was dark brown in color, showed a low yield of biphenol and the presence of other unidentified materials. Run No. 2, the reactants for which contained no catalyst but included the initial addition of water, showed no initial reaction inhibition period but did exhibit a very slow reaction rate. The crude reaction product was dark brown in color and showed a low yield of biphenol plus the presence of other unidentified materials.

In Run No. 8, a high initial temperature (224° C.) was employed and while the initial reaction rate was fast, the reaction stopped after a short time (oxygen uptake came to a complete stop). The crude reaction product was a dark brown and biphenol yield was lower than expected, but nothing further unusual was observed.

EXAMPLE 4

A. A pressure reaction vessel equipped with stirrer, air delivery tube, and heating means, and pressure gauge and venting valve was used in this Example. A solution of 103 grams of 2,6-di-tert.butyl phenol in 345 grams of toluene was charged into the reaction vessel and 6.5 grams of an 86 percent potassium hydroxide solution was added. The reactor was sealed and, while stirring the reactants, heated to 70° C. Air was passed through the liquid phase in the reactor at a rate of 3 liters (STP) per minute and spent air was vented from the vapor phase in the reactor at a controlled rate such that the pressure within the reactor was maintained at about 300 psig. After a reaction time of 40 minutes, the air flow and heating were stopped and the reactor was allowed to cool. When cooled, the reactor was vented and the contents thereof were discharged. Analysis of the crude reaction product showed that 31 percent of the substituted phenol had been converted to the corresponding dimer with substantially no quinone being found.

B. Using the procedure and proportion of reactants hereinabove described, a reaction was carried out by passing air through the liquid components and heating for 2 hours. The crude reaction product after a reaction time of 2 hours was found to contain only the corresponding diphenyl quinone and no amount of biphenol dimer. About 68 percent of the substituted phenol was converted during the reaction.

C. A solution of 103 grams of 2,6-di-tert.butyl phenol in 345 grams of toluene, 6.9 grams of potassium carbonate and 1.2 grams of water were reacted using the procedure hereinabove described. After a reaction time of 2 hours, there was no evidence of the substituted phenol being converted to either the corresponding dimer or diphenoquinone.

The importance of limiting the amount of oxidant during the oxidation of a substituted phenol to obtain the corresponding biphenol is readily apparent from Reaction A and B of this Example. Moreover, in Reaction C is shown the importance of the choice of catalyst to be employed.

EXAMPLE 5

By a procedure analogous to that described in Example 3, a series of reactions were carried out using the following proportion of reactants, pressure and temperature ranges, and reaction times.

| Run | DTBP (grams) | Catalyst (grams) | Water (grams) | Temp. Range (°C.) | Pressure Range (psig) | Time (min) |
|-----|-----|-----|-----|-----|-----|-----|
| 1 | 500 | 7 | 0 | 187–195 | 70–200 | 35 |
| 2 | 500 | 0.6 | 10 | 189–214 | 175–200 | 26 |
| 3 | 500 | 7.1 | 10 | 190–224 | 125–225 | 38 |
| 4 | 500 | 8.6 | 0 | 190–220 | 100–150 | 36 |
| 5 | 500 | 0.78 | 0.75 | 190–220 | 175–200 | 29 |

The following materials were employed as catalyst in the various reactions of this example:
Run No. 1 diazabicyclonanane
Run No. 2 pyridine
Run No. 3 pyridine
Run No. 4 $Na_2B_2O_7 \cdot 10H_2O$
Run No. 5 potassium acetate During each of the reaction runs of this example, a crude reaction was recovered, analysis of which showed conversion of from about 25 percent to about 40 percent of the substituted phenol to the corresponding dimer and substantially no quinones.

EXAMPLE 6

A continuous reactor tube one inch in diameter (I.D.) and 68.5 inches long having a pressurized water jacket, heating means, and insulation was packed with 1308 grams of 0.160 inch, type 316 stainless steel protruded metal packing (available under trade name "Pro-Pak" from Scientific Development Co., State College, Pa.). Means were provided for separately pumping substituted phenol, catalyst solutions, and water as needed. Compressed air was injected at the column top in order to provide for co-current, down-flow mode of operation. The gas and liquid stream from the reactor was separated at the reactor bottom and exited through appropriate control valves. The proportion of reactants, reactor pressure and temperature, and biphenol yield for a series of reactions are reported in Table I, below.

From the results obtained, the nature and color of biphenol products prepared using either potassium carbonate or 1,4-diazabicyclooctane (DABCO) catalyst were similar. In each case the product obtained was light tan in color and contained only the corresponding biphenol with no quinone being in evidence. The somewhat lower conversion of phenol to biphenol in Run No. 1 is attributed to the induction time for initiating the reaction since no water was added to the initial reactant mixture.

TABLE I

| Run No. | Di-Tert. Butyl Phenol (grams/hour) | Catalyst Type | Catalyst Rate (grams/hour) | Water (grams/hour) | Air (liters(STP)/hour) | Reactor Temp. (°C.) | Reactor Pressure (psig) | Biphenol (%) | Exit Gas (Volume % $O_2$) |
|---|---|---|---|---|---|---|---|---|---|
| 1 | 775 | DABCO[1] | 7.8[2] | 0 | 150 | 194–206 | 200 | 15 | 4.5 |
| 2 | 750 | DABCO[1] | 7.8[2] | 110 | 80 | 197–206 | 200 | 20–38 | 10–13 |
| 3 | 750 | $K_2CO_3$ | 60[3] | [3] | 60 | 196–204 | 200 | 26 | 2–3 |
| 4 | 630 | $K_2CO_3$ | 50[3] | [3] | 120–150 | 200–208 | 200 | 40–60 | 6–11 |

[1] 1,4-diazabicylooctane
[2] the catalyst was added by dissolving in the DTBP feed
[3] 10% aqueous solution of $K_2CO_3$

What is claimed is:

1. A process for making 4,4'-bis(2,6-di-substituted-phenols) which comprises intimately contacting a phenol having the formula

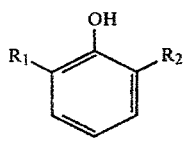

wherein $R_1$ and $R_2$ may be the same or different and is a member selected from the group consisting of alkyl radicals containing from 1 to 20 carbon atoms, aryl radicals containing from 6 to 14 carbon atoms, aralkyl radicals containing from 7 to 9 carbon atoms, and cyclic alkyl groups, with up to a stoichiometric amount of oxygen or an oxygen containing gas in the presence of a catalytic quantity of a catalyst consisting essentially of a member selected from alkali metal hydroxides, alkali metal salts of a weak acid, alkaline earth metal hydroxides, alkaline earth metal salts of a weak acid, amine bases, and mixtures of the same at an elevated temperature for the time necessary to react up to a stoichiometric amount of oxygen with said phenol to form a reaction product containing a substantial amount of 4,4'-bis(2,6-disubstituted phenol).

2. The process of claim 1 wherein said reaction product is substantially free of quinones.

3. The process of claim 1 wherein at least about 0.01 weight percent of water or a lower hydroxyl containing alkyl compound, based on the weight of reaction mixture, is added as an initial reaction component.

4. The process of claim 1 wherein said reaction is carried out at a temperature of from at least the melting point of the reaction mixture to about 220° C.

5. The process of claim 1 wherein there is present at least about 0.1 weight percent of said catalyst.

6. The process of claim 5 wherein there is present up to about 1 weight percent of said catalyst.

7. The process of claim 1 wherein said catalyst is selected from the group consisting of alkali metal salts of a weak acid, alkaline earth metal salts of a weak acid, amine bases, and mixtures of the same.

8. A process for making 4,4'-bis(2,6-di-hydroxycarbylphenols) which comprises reacting with good agitation a ratio of 4 moles of a phenol having the formula

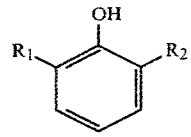

wherein $R_1$ and $R_2$ may be the same or different and is a member selected from the group consisting of alkyl radicals containing from 1 to 20 carbon atoms, aryl radicals containing from 6 to 14 carbon atoms, aralkyl radicals containing from 7 to 9 carbon atoms, and cyclic alkyl groups with up to 1 mole of oxygen in the presence of at least a small catalytic quantity of a catalyst consisting essentially of a member selected from alkali metal hydroxides, alkali metal salts of a weak acid, alkaline earth metal hydroxides, alkaline earth metal salts of a weak acid, amine bases, and mixtures of the same at a temperature of from about 50° to about 240° C. until a reaction product containing a substantial amount of 4,4'-bis(2,6-di-hydrocarbylphenol) is formed.

9. The process of claim 8 wherein said reaction is carried out in the presence of at least about 0.1 weight percent of said catalyst.

10. The process of claim 9 wherein said reaction is carried out in the presence of up to about 1 weight percent of said catalyst.

11. The process of claim 8 wherein said reaction is carried out at a temperature of from about the melting point of the reaction mixture to about 220° C.

12. The process of claim 11 wherein said reaction mixture is substantially free of any solvent.

13. The process of claim 8 wherein at least about 0.01 weight percent of water or a lower hydroxyl containing alkyl compound, based on the weight of reaction mixture, is added as an initial reaction component.

14. The process of claim 8 wherein said reaction is carried out until substantially all of said phenol is reacted.

15. The process of claim 8 wherein said catalyst is selected from the group consisting of alkali metal salts of a weak acid, alkaline earth metal salts of a weak acid, amine bases, and mixtures of the same.

16. The process of claim 8 wherein said phenol is 2,6-di-tertiary-butyl phenol and the reaction product formed therefrom is the corresponding 4,4'-biphenol.

* * * * *